(12) United States Patent
Lee et al.

(10) Patent No.: US 7,902,190 B2
(45) Date of Patent: Mar. 8, 2011

(54) INDOL DERIVATIVES, THE METHOD FOR PREPARING THEREOF AND COMPOSITION FOR THE PREVENTION AND TREATMENT OF METABOLIC DISORDER CONTAINING THE SAME AS AN ACTIVE INGREDIENT

(75) Inventors: Kyeong Lee, Taejeon-si (KR); Hyun Sun Lee, Taejeon-si (KR); Jung Joon Lee, Taejeon-si (KR); Young Kook Kim, Taejeon-si (KR); Mun-Chual Rho, Taejeon-si (KR); Jeong Hyung Lee, Taejeon-si (KR); Hye-Ran Park, Kyeonggi-do (KR); Chul-Ho Lee, Taejeon-si (KR); Yongseok Choi, Seoul (KR)

(73) Assignee: Korea Research Institute of Bioscience and Biotechnology, Daejeon-Si (KR)

( * ) Notice: Subject to any disclaimer, the term of this patent is extended or adjusted under 35 U.S.C. 154(b) by 131 days.

(21) Appl. No.: 12/442,930

(22) PCT Filed: Sep. 27, 2007

(86) PCT No.: PCT/KR2007/004722
§ 371 (c)(1), (2), (4) Date: Mar. 25, 2009

(87) PCT Pub. No.: WO2008/039007
PCT Pub. Date: Apr. 3, 2008

(65) Prior Publication Data
US 2010/0075962 A1 Mar. 25, 2010

(30) Foreign Application Priority Data
Sep. 27, 2006 (KR) .................. 10-2006-0094138

(51) Int. Cl.
A61K 31/535 (2006.01)
(52) U.S. Cl. .................. 514/235.2; 548/469; 514/254.09
(58) Field of Classification Search ............... 514/235.2, 514/254.09; 548/469
See application file for complete search history.

(56) References Cited

U.S. PATENT DOCUMENTS

| 6,432,682 B1 | 8/2002 | Omura et al. |
| 6,608,185 B1 | 8/2003 | Omura et al. |

FOREIGN PATENT DOCUMENTS

| KR | 0460438 | 6/2003 |
| KR | 0577320 | 4/2004 |
| KR | 0507989 | 7/2004 |
| WO | WO 99/35130 | 7/1999 |
| WO | WO2004/046107 | 6/2004 |
| WO | WO 2005094816 A1 * | 10/2005 |
| WO | WO2006/004200 | 1/2006 |
| WO | WO2006/019020 | 2/2006 |
| WO | WO2006/044775 | 4/2006 |

OTHER PUBLICATIONS

Chen et al. (2002) "Increased insulin and leptin sensitivity in mice lacking acyl CoA:diacylglycerol acyltransferase 1," *J. Clin. Invest.*, 109(8), 1049-1055.
Chen, H.C., et al. (2000) "DGAT and Triglyceride Synthesis: A New Target for Obesity Treatment?" *Trends Cardiovasc. Med.*, 10, 188-192.
Chen et al. (2003) "Obesity resistance and enhanced glucose metabolism in mice transplanted with white adipose tissue lacking acyl CoA:diaclyglycerol acyltransferase," *J. Clin. Invest.*, 111, 1715-1722.
Chen et al. (2003) "Anaysis of energy expenditure at different ambient temperatures in mice lacking DGAT1," *Am. J. Physiol. Endocronol. Metab.*, 284, E213-218.
Chen et al.(2005) "Inhibition of Triglyceride Synthesis as a Treatment Strategy for Obesity: Lessons From DGAT1-Deficient Mice," *Arterioscler Thromb Vasc. Biol.* 25(3), 482-486.
Chen et al. (2002), "Dissociation of Obesity and Impaired Glucose Disposal in Mice Overexpressing Acyl Coenzyme A:Diacylglycerol Acyltransferase 1 in White Adipose Tissue," *Diabetes.* 51(11), 3189-3195.
Ganji et al. (2004) "Niacin noncompetitively inhibits DGAT2 but not DGAT1 activity in HepG2 cells," *Journal of Lipid Research* 45:1835-1845.
Rustan et al. (1988) "Eicosapentaenoic acid reduces hepatic synthesis and secretion of triacyglycerol by decreasing the activity of acyl-coenzyme A:1,2-diacylglycerol acyltransferase," *Journal of Lipid Research* 29:1417-1426.
Smith, S.J. et al.(2000) "Obesity resistance and multiple mechanisms of triglyceride synthesis in mice lacking Dgat," *Nature genetics*, 25, 87-90.
Subauste et. al. (2003) "DGAT: Novel Therapeutic Target for Obesity and Type 2 Diabetes Mellitus," *Current Drug Target-Immun2, Endocrine & Metabol Disorders*, 3, 263-270.
Yoganathan et al. (2004) "Cochlioquinones and Epi-Cochlioquinones Antagonists of the Human Chemokine Receptor CCR5 from Bipolaris brizae and *Stachybotrys chartarum*," *The Journal of Antibiotics* 57,1:59-63.
International Search Report and Written Opinion dated Jan. 7, 2008 for PCT/KR2007/00722.

* cited by examiner

Primary Examiner — Brandon J Fetterolf
Assistant Examiner — Jean Cornet
(74) *Attorney, Agent, or Firm* — Greenlee Sullivan P.C.

(57) ABSTRACT

Disclosed are indole derivatives, a preparation method thereof, and a composition for the prevention and treatment of metabolic diseases, containing the same as an active ingredient. The indole derivatives have inhibitory activity against DGAT (diacylglycerol acyltransferase), which causes metabolic diseases such as obesity and diabetes in the process of lipid metabolism. With the ability to effectively control lipid metabolism and energy metabolism, the composition is thus useful in the prevention and treatment of metabolic diseases, such as obesity and diabetes.

11 Claims, No Drawings

INDOL DERIVATIVES, THE METHOD FOR PREPARING THEREOF AND COMPOSITION FOR THE PREVENTION AND TREATMENT OF METABOLIC DISORDER CONTAINING THE SAME AS AN ACTIVE INGREDIENT

CROSS-REFERENCE TO RELATED APPLICATIONS

This application is the U.S. National Stage of International Application No. PCT/KR2007/004722, filed Sep. 27, 2007, which claims the benefit of Korean Patent Application KR10-2006-0094138, filed Sep. 27, 2006, both of which are hereby incorporated by reference to the extent not inconsistent with the disclosure hereof.

TECHNICAL FIELD

The present invention relates to indole derivatives, a method for preparing thereof and a composition for the prevention and treatment of metabolic disorders containing the same as an active ingredient.

BACKGROUND ART

Acyl CoA: diacylglycerol acyltransferase (hereinafter referred to as "DGAT") is an integral membrane enzyme that catalyses the last step of the glycerol 3-phosphate pathway, synthesizing triacylglycerol from the substrates sn-1,2-diacylglycerol and fatty acyl CoA. As a rule, the biosynthesis of triacylglycerol is accomplished through the glycerol 3-monophosphate pathway (the liver and adipose tissues) and the monoacylglycerol pathway (intestinal epithelial cells).

Recently, at the Gladstone Institute of Cardiovascular Diseases, U.S.A., DGAT-1 gene deficient mice have been used in the study of DGAT functions, yielding evidence that DGAT-1 deficient mice are protected from diet-induced obesity even when they are weaned on a high-fat diet, and that DGAT-1 deficiency enhances insulin and leptin deficiency, improving glucose metabolism. A subsequent research result showed that the selective inhibition of DGAT, an enzyme that catalyzes the biosynthesis of triglycerides in insulin-sensitive tissues, such as adipose tissues, skeletal muscles, the liver, beta cells of the pancreas, etc., is useful in the prevention and treatment of obesity and type II diabetes mellitus (Chen H C, et al., *Trends Cardiovasc. Med.*, 10, 188-192, 2000; Farese Jr. et al., *Curr. Opin. Lipidol.*, 11, 229-234, 2000; A. Subauste et. al., *Currunt Drug Target-Immun, Endocrine & Metabol Disorders*, 3, 263-270, 2003; Y. Yu et. al. *Annals of Medicine*, 36. 252-261).

Decreased activity of DGAT results in the blockage of enzymatic reactions for triglyceride biosynthesis or a reduction in biosynthesis yield. When the biosynthesis of triglyceride is restricted by inhibiting DGAT, an enzyme participating in the final step of triglyceride biosynthesis, there are a decrease in the accumulation of fats in adipose tissues, a decrease in the size of adipose cells, and an increase in energy expenditure attributable to increased ambulatory physical activity and increased expression of uncoupling proteins, thereby giving rise to resistance to diet-induced obesity (Smith S J. et al., *Nature genetics*, 25, 87-90, 2000; Chen et al., *J Clin Invest.*, 109(8), 1049-1055, 2002; Chen et al., *J Clin Invest.*, 111, 1715-1722, 2003; Chen et al. *Am. J. Physiol. Endocronol. Metab.*, 284, E213-218, 2003).

In addition, it is known that the inhibition of DGAT restricts the accumulation of fats in non-adipose tissues, such as the skeletal muscles, the liver, the pancreas and the like, leading to an improvement in insulin resistance.

Insulin stimulation results in decreased serine inhibitory phosphorylation and tyrosine phosphorylation of IRS-(insulin receptor substance-1), and increased insulin signaling transduction through PI-3K (phosphatidylinositol-3 kinase), PKB (protein kinase B, Akt) and PKC$_\lambda$ (protein kinase C$_\lambda$), thereby increasing the number of the glucose transporter GLUT-4.

When the activity of DGAT within cells is decreased, the activities of PI-3K, PKB and PKC$_\lambda$ increase, thus stimulating GLUT-4 exocytosis and increasing the amount of glucose introduced into the cells. In other words, the inhibition of DGAT activity enhances insulin sensitivity (Chen et al., *Arterioscler Thromb Vasc Biol.* 25(3), 482-486, 2005; Chen et al., *J Clin Invest.* 111(11), 1715-22, 2003; Chen et al., *J Clin Invest.* 109(8), 1049-1055, 2002; Chen et al., *Diabetes.* 51(11), 3189-3195, 2002; Subauste and Burant., *Curr Drug Targets Immune Endocr Metabol Disord.* 3(4), 263-270, 2003). With the discovery of the correlation between the inhibition of DGAT and the subjugation of insulin resistance, DGAT arises as a therapeutic target for type II diabetes mellitus, which is characterized by the obstruction of glucose absorption due to insulin resistance, but with normal insulin secretion.

Synthetic chemicals known as DGAT inhibitors include biphenyl-4-yl-carbonylaminoacid derivatives (WO2006044775, Bayer Pharmaceuticals Corp), urea derivatives (WO2006019020, WO2006004200, Sankyo Co), pyrrolecarboxylic acid derivatives (JP05213985A, Mitsubishi Kasei Corp, Japan) and phosphonic acid ester derivatives (JP2004067635A, Otsuka Pharmaceut Factory Inc., Japan). DGAT inhibitors in the form of naturally occurring materials include polyacetylenes from Ginseng (Korean Patent No. 0460438, Lee et al. *Planta Med.* 70, 179-200, 2004), quinolone alkaloids, tanshinones, prenylflavonoids isolated from *Evodia officinalis, Salvia miltiorrhiza* BUNGE, and *Sophora flavescens* (Korean Pat. No. 0577320, Ko et al., *Arch. Phar. Res.* 25, 446-448, 2002, Korean Patent No. 0507989).

Also reported as DGAT inhibitors are roselipins (U.S. Pat. Nos. 6,432,682 (2002) and 6,608,185 (2003)) (Omura et al., the Kitasato Institute and Graduate School of Pharmaceutical Sciences), cochlioquinone A and A1 (*J. Antibiot.*, 56, 967, 2003; *J. Antibiot.*, 57, 59, 2004), amidepsines and xanthohumol. Other examples include eicosapentaenoic acid, 2-bromooctanoate and niacin (Rustan et al., *J. Lipid. Res.*, 29, 1417-1426, 1988, Ganji et al. *J. Lipid. Res.*, 45, 1835-1845).

Leading to the present invention, intensive and thorough research into active materials inhibitory of DGAT, conducted by the present inventors, resulted in the finding that indole derivatives inhibit the biosynthesis of triglycerides to bring about various effects including the prevention of diet-induced obesity, the amelioration of blood lipid levels, and the prevention of fat accumulation in adipose cells, and thus can be applied to the treatment of metabolic disorders, such as obesity, diabetes and the like.

DISCLOSURE

Technical Problem

It is an object of the present invention to provide novel indole derivatives useful in the prevention and treatment of metabolic disorders.

It is another object of the present invention to provide a method for preparing the indole derivarives.

It is a further object of the present invention to provide a composition for the prevention and treatment of metabolic disorders, comprising the novel indole derivatives as an active ingredient.

Technical Solution

In order to accomplish the above objects, the present invention provides indole derivatives, a preparation method thereof, and a composition for the prevention and treatment of metabolic disorders, containing the same.

ADVANTAGEOUS EFFECTS

The indole derivatives according to the present invention effectively inhibit diacylglycerol acyltransferase (DGAT), an enzyme which may cause metabolic disorders, such as obesity and diabetes, in the process of lipid metabolism, and thus can be used as a therapeutic for the treatment of metabolic disorders, such as obesity and diabetes.

BEST MODE

In accordance with an aspect thereof, the present invention provides a novel indole derivative represented by the following Chemical Formula 1:

[Chemical Formula 1]

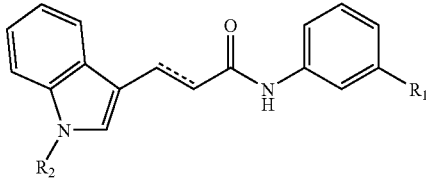

wherein, $R_1$ is one selected from a group consisting of $COOR_a$, $CONR_bR_c$ and $C_1\sim C_4$ alkyl, wherein $R_a$ is H or $C_1\sim C_4$ alkyl, and $R_b$ and $R_c$ are independently selected from a group consisting of $C_1\sim C_5$ alkyl bearing a 5~7 atom-membered heteroalkyl group containing N, O or S or a 5~7 atom-membered heterocyclic group containing N, O or S; H; and $C_1$-$C_s$ alkyl;

$R_2$ is selected from a group consisting of $C_5\sim C_7$ aryl $C_1\sim C_5$ alkyl, di-$C_1\sim C_5$ alkylamino $C_1\sim C_5$ alkyl, $C_1\sim C_5$ alkylcarbonyl, $C_1\sim C_5$ alkyl $C_1\sim C_5$ alkoxycarbonyl, $C_5\sim C_7$ aryl $C_1\sim C_5$ alkylsulfonyl, and thiophene $C_1\sim C_5$ alkylsulfonyl; and the symbol ≡≡≡ designates a single bond or a double bond.

In a preferable embodiment, $R_1$ is selected from a group consisting of aminocarbonyl; methoxycarbonyl; hydroxycarbonyl; 2-piperidin-1-yl-ethylaminocarbonyl; 3-morpholin-4-yl-propylaminocarbonyl; and furan-2-yl-methylaminocarbony, $R_2$ is selected from a group consisting of H; butoxycarbonyl; benzyl; N,N-dimethyl-2-aminoethyl; acetyl; thiophene-2-sulfonyl; phenylmethanesulfonyl; and t-butoxycarbonylmethyl.

Concrete examples of the indole derivatives represented by Chemical Formula 1 in accordance with the present invention include:

1) 3-(3-1H-indol-3-yl-propionylamino)-benzamide;
2) 3-(3-1H-indol-3-yl-acryloylamino)-benzamide;
3) 3-(3-1H-indol-3-yl-propionylamino)-benzoic acid methyl ester;
4) 3-(3-1H-indol-3-yl-acryloylamino)-benzoic acid methyl ester;
5) 3-(3-1H-indol-3-yl-propionylamino)-benzoic acid;
6) 3-(3-1H-indol-3-yl-acryloylamino)-benzoic acid;
7) 3-(3-1H-indol-3-yl-acryloylamino)-(2-piperidin-1-yl-ethyl)-benzamide;
8) 3-(3-1H-indol-3-yl-acryloylamino)-(3-morpholin-4-yl-propyl)-benzamide;
9) N-furan-2-ylmethyl-3-(3-1H-indol-3-yl-acryloylamino)-benzamide;
10) 3-(2-3-[(furan-2-ylmethyl)-carbamoyl]-phenylcarbamoyl-vinyl)-indole-1-carboxylic acid t-butyl ester;
11) 3-[3-(1-benzyl-1H-indol-3-yl)-acryloylamino]-N-furan-2-ylmethyl-benzamide;
12) 3-{3[1-(2-dimethylamino-ethyl)-1H-indol-3-yl]-acryloylamino}-N-furan-2-ylmethyl-benzamide;
13) [3-(2-{3-[(furan-2-ylmethyl)-carbamoyl]-phenylcarbamoyl}-vinyl)-indol-1-yl]-acetic acid t-butyl ester;
14) N-furan-2-ylmethyl-3-[3-(1-phenylmethanesulfonyl-1H-indol-3-yl)-acryloylamino]-benzamide;
15) N-furan-2-ylmethyl-3-{3-[1-(thiophene-2-sulfonyl)-1H-indol-3-yl]-acryloylamino}-benzamide; and
16) 3-[3-(1-acetyl-1H-indol-3-yl)-acryloylamino]-N-furan-2-ylmethyl-benzamide.

The derivatives of Chemical Formula 1 are summarized with regard to the structures $R_1$ and $R_2$ in Table 1, below.

TABLE 1

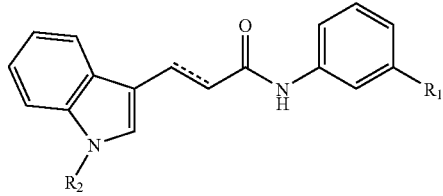

| Cpd. | $R_1$ | $R_2$ | Bond |
|---|---|---|---|
| 1 | $CONH_2$ | H | Single |
| 2 | $CONH_2$ | H | Double |
| 3 | $COOCH_3$ | H | Single |
| 4 | $COOCH_3$ | H | Double |
| 5 | COOH | H | Single |
| 6 | COOH | H | Double |

TABLE 1-continued

| Cpd. | R₁ | R₂ | Bond |
|------|----|----|------|
| 7 | piperidinyl-ethyl-NH-C(=O)- | H | Double |
| 8 | morpholinyl-propyl-NH-C(=O)- | H | Double |
| 9 | furan-2-yl-methyl-NH-C(=O)- | H | Double |
| 10 | furan-2-yl-methyl-NH-C(=O)- | tert-butyl ester | Double |
| 11 | furan-2-yl-methyl-NH-C(=O)- | benzyl | Double |
| 12 | furan-2-yl-methyl-NH-C(=O)- | dimethylamino-ethyl | Double |
| 13 | furan-2-yl-methyl-NH-C(=O)- | tert-butyl ester (CH₂) | Double |
| 14 | furan-2-yl-methyl-NH-C(=O)- | Ph-CH₂-S(=O)₂- | Double |
| 15 | furan-2-yl-methyl-NH-C(=O)- | thiophen-2-yl-S(=O)₂- | Double |

TABLE 1-continued

| Cpd. | R₁ | R₂ | Bond |
|---|---|---|---|
| 16 | (furan-2-ylmethyl)carbamoyl | acetyl (Me-C(=O)-) | Double |

Also, the indole derivatives represented by Chemical Formula 1 may be used in the form of pharmaceutically acceptable salts. The pharmaceutically acceptable salts useful in the present invention may be addition salts of acceptable free acids. Organic or inorganic acids may be used for the formation of acid addition salts. Suitable as inorganic acids are hydrochloric acid, bromic acid, sulfuric acid and phosphoric acid. Examples of suitable organic acids include citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, galacturonic acid, embonic acid, glutamic acid, and aspartic acid.

Furthermore, the present invention includes hydrates and solvates of the benzazole derivatives of Chemical Formula 1, and salts thereof.

In accordance with another aspect thereof, the present invention provides a method for preparing the novel indole derivatives of Chemical Formula 1.

The indole derivatives of Chemical Formula 1 for use in the prevention and treatment of metabolic disorders can be synthesized as elucidated in Reaction Scheme 1, below. The method comprises a condensation reaction between a starting material 3-(1H-indol-3-yl)propionic acid of Chemical Formula 2 and an amine derivative bearing an R₁ substituent of Chemical Formula 3 at room temperature in an organic solvent with the aid of a condensing agent in the presence of a base to produce a compound of Chemical Formula 1a.

[Reaction Scheme 1]

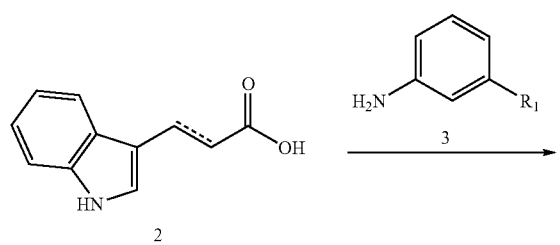

-continued

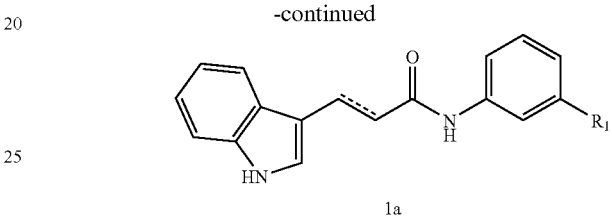

1a (wherein, R₁ is as defined in Chemical Formula 1, and the compound of Chemical formula 1a is included in the indole derivatives of Chemical Formula 1)

Particularly, when the amine derivative of Chemical Formula 3 in Reaction Scheme 1 bears —COOR$_a$ as the substituent R₁, the indole derivatives of Chemical Formula 1 in accordance with the present invention can be synthesized, as elucidated in Reaction Scheme 2, below, through a series of reactions including condensation via an amide bond, de-esterification, another condensation via an amide bond, and substitution with a halogenide or anhydride bearing R₂.

When R₁ is —COOR$_a$, the indole derivatives of Chemical Formula 1 in accordance with the present invention can be prepared, as shown in Reaction Scheme 2, using a method comprising:

condensing the starting material 3-(1H-indol-3-yl)propionic acid of Chemical Formula 2 with an amine derivative bearing —COOR$_a$ as R₁ of Chemical Formula 4 at room temperature in the presence of a base and a condensing reagent in an organic solvent to produce a derivative of Chemical Formula 1b in which the propionic acid and the amine derivative is coupled via an amide bond (Step 1);

de-esterifying the derivative of Chemical Formula 1b into a derivative of Chemical Formula 1c at room temperature in the presence of a base in an organic solvent/water mixture (Step 2); condensing the derivative of Chemical Formula 1c with alkyl amine (HNR$_b$R$_c$) at room temperature or flux under the same conditions as in Step 1, including the solvent, the base and the condensing reagent to produce a derivative of Chemical Formula 1d in which the two reactants are coupled via an amide bond (Step 3); and introducing R2 onto the nitrogen atom of the derivative of Chemical Formula 1d in the presence of a base in an organic solvent to produce a derivative of Chemical Formula 1e (Step 4).

[Reaction Scheme 2]

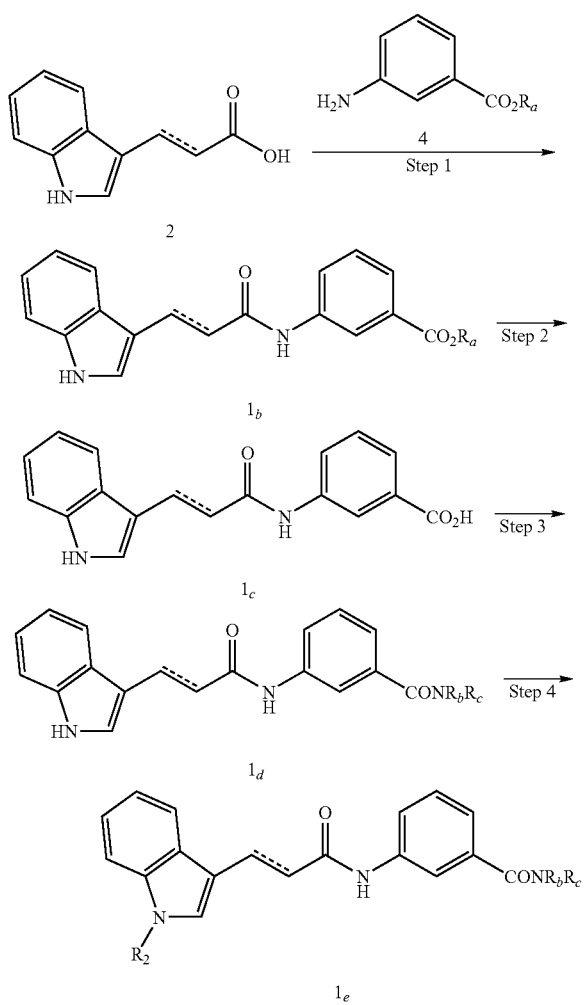

(wherein, $R_a$, $R_b$, $R_c$ and $R_2$ are as defined in Chemical Formula 1, and the derivatives of Chemical Formulas 1b to 1e are included in the indole derivatives of Chemical Formula 1 in accordance with the present invention)

The preparation method of the present invention is explained in a stepwise manner below.

In the preparation step shown in Reaction Scheme 1 or Step 1 shown in Reaction Scheme 2, the starting material 3-(1H-indol-3-yl)propionic acid of Chemical Formula 2 is condensed with the amine derivative of Chemical Formula 3 or 4 to give the derivative of Chemical Formula 1a or 1b.

The starting material 3-(1H-indol-3-yl)propionic acid of Chemical Formula 2 is commercially available or may be synthesized using a well known technique.

Also, the amine derivative used in this step is commercially available or may be synthesized using a well known technique. Preferable examples of the amine derivative include 3-amino-benzamide and 3-amino-benzoic acid methyl.

Useful for use as the organic solvent in this step is dimethylformamide or methylenechloride. Diisopropylamine or triethylamine may be used as the base.

For use in the condensation via an amide bond, a condensing reagent is known as a peptide coupling reagent, examples of which include benzotriazol-1-yl-oxytripyrrolidino-phosphonium hexafluorophosphate (PyBOP), ethylenedichloride (EDC), N-hydroxybenzotriazole (HOBt), O-(benzotriazol-1-yl)-1,1,3,3-tetramethyl uronium hexafluorophosphate (HBTU), and O-(7-azabenzotriazol-1-yl)-N,N,N',N'-tetramethyl uronium hexafluorophosphate (HATU).

In Step 2 of Reaction Scheme 2, the derivative of Chemical Formula 1e, produced in Step 1, is de-esterified into the derivative of Chemical Formula 1c, which falls within the scope of the indole derivatives of Chemical Formula 1.

This de-esterification is performed in the presence of a base in a solvent. Lithium hydroxide or sodium hydroxide may be used as the base. Preferably, an organic solvent, such as tetrahydrofuran, dioxane, methanol or ethanol, may be used alone or in combination with water.

In Step 3 for condensation, the derivative of Chemical 1c, produced in Step 2, is coupled to alkylamine ($HNR_bR_c$) to produce a derivative of Chemical Formula 1d, which is included within the scope of the indole derivatives of Chemical Formula 1.

This condensation of Step 3 may be performed under the same conditions as in Reaction Scheme 1 or Step 1 of Reaction Scheme 2. The same solvent, base and condensing reagent as used in Reaction Scheme 1 or Step 2 can be employed in this condensation. The reaction may be performed at room temperature, and optionally with reflux.

The alkylamine bearing $R_b$ and $R_c$ (—$HNR_bR_c$) may be a commercially available one, or may be synthesized using well known techniques. Examples of the alkyl amine useful in this condensation include 2-perfurylamine, 2-piperidin-1-yl-ethylamine, and 3-morpholin-4-yl-propylamine.

In Step 4, $R_2$ is introduced from a halogenide or anhydride bearing $R_2$ onto the derivative of Chemical Formula 1d through a substitution reaction to give a derivative of Chemical formula 1e.

This substitution reaction is carried out in the presence of a base, such as anhydrous potassium carbonate or anhydrous cesium carbonate, in a solvent, such as dimethylformamide or methylenechloride.

Useful as the halogenide or anhydride which bears $R_2$ is benzyl bromide, 2-dimethylaminoethyl chloride, benzyl sulfonyl chloride, 2-thiophenesulfonyl chloride, t-butyl bromoacetate, di-t-butoxydicarbonate, or acetic acid anhydride.

Preferably, the substitution reaction is carried out at room temperature for about 12 hours.

Alternatively, the indole derivatives of Chemical Formula 1 may be prepared through other synthesis routes, in which the reaction orders of Steps 1 to 4 in Reaction Scheme 2 are properly changed.

In accordance with a further aspect thereof, the present invention provides the use of the indole derivatives represented by Chemical Formula 1 or pharmaceutically acceptable salts thereof.

With ability to inhibit DGAT, a composition comprising an indole derivative represented by Chemical Formula 1 or a pharmaceutically acceptable salt thereof as an active ingredient can be used as a therapeutic for the treatment of metabolic disorders, such as obesity and diabetes.

Using sn-1,2-diacylglycerol and fatty acyl CoA as substrates, DGAT is an integral membrane enzyme that catalyses the final step of the glycerol 3-phosphate pathway to synthesize triacylglycerol. Typically, triglyceride biosynthesis follows the glycerol 3-monophosphate pathway (the liver and adipose tissues) and the monoacylglycerol pathway (intestinal epithelial cells).

The inhibition of triglyceride biosynthesis is reported to result in the suppression of fat accumulation in adipose tissues, a decrease in the size of adipose cells, the stimulation of adiponectin secretion from adipose cells, an increase in ambulatory physical activity, and resistance to diet-induced obesity (Smith S J. et al., *Nature genetics,* 25, 87-90, 2000; Chen et al., *J Clin Invest.,* 109(8), 1049-1055, 2002; Chen et al., *J Clin Invest.,* 111, 1715-1722, 2003; Chen et al. *Am. J. Physiol. Endocrinol. Metab.,* 284, E213-218, 2003).

Also, DGAT inhibition is known to suppress the accumulation of fats in non-adipose tissues, such as the skeletal muscles, the liver, the pancreas and the like, thereby giving rise to an improvement in insulin resistance.

Upon insulin stimulation, the serine inhibitory phosphorylation of IRS-1 (insulin receptor substance-1) decreases with an increase in the activity of insulin signal transduction through PI-3K (phosphatidylinositol-3 kinase), PKB (protein kinase B, Akt) and $PKC_\lambda$ (protein kinase $C_\lambda$), to stimulate GLUT-4 (glucose transporter-4) exocytosis and thus stimulate the introduction of glucose into cells. In other words, the inhibition of DGAT activity enhances insulin sensitivity to thus improve insulin resistance (Chen et al., *Arterioscler Thromb Vasc Biol.* 25(3): 482-486, 2005; Chen et al., *J Clin Invest.* 111(11): 1715-22, 2003; Chen et al., *J Clin Invest.* 109(8): 1049-1055, 2002; Chen et al., *Diabetes.* 51(11): 3189-3195, 2002; Subauste and Burant., *Curr Drug Targets Immune Endocr Metabol Disord.* 3(4): 263-270, 2003).

Accordingly, DGAT inhibitors are applicable in the prevention and treatment of metabolic disorders, such as obesity and diabetes. There are many research results reporting action as DGAT inhibitors (Chen H C, et al., *Trends Cardiovasc. Med.,* 10, 188-192, 2000; Farese Jr. et al., *Curr. Opin. Lipidol.,* 11, 229-234, 2000; A. Subauste et. al., *Current Drug Target-Immun, Endocrine & Metabol Disorders,* 3, 263-270, 2003; Y. Yu et. al. *Annals of Medicine,* 36. 252-261; Hubert C. et al., *Arterioscler. Thromb. Vasc. Biol.,* 25, 1-5, 2005; Smith S J. et al., *Nature genetics,* 25, 87-90, 2000).

The indole derivatives of Chemical Formula 1 in accordance with the present invention are found to effectively inhibit the enzymatic activity of DGAT in a dose-dependent manner (refer to Table 2) as measured in a test in which [$^{14}$C]triacylglycerol was quantitatively analyzed after enzymatic reaction between 1,2-diacylglycerol and [$^{14}$C]palmitoyl-CoA, with microsomal proteins from rats serving as an enzyme source (refer to Experimental Example 1).

In addition, the compounds (10, 11 and 15) of Chemical Formula 1 were observed to highly inhibit the biosynthesis of triglyceride (refer to Table 3) in comparison with the control, as analyzed in a test in which the derivatives of Chemical Formula 1 were measured for inhibitory activity against DGAT after the treatment of HepG2 with the derivatives (refer to Experimental Example 2). Therefore, it is speculated that the inhibition of these compounds occurs within the cells as they enter the cells.

Demonstrated to have potent inhibitory activity against DGAT in vitro and on triglyceride biosynthesis in vivo, the composition comprising a derivative of Chemical Formula 1 or a pharmaceutically acceptable salt thereof as an active ingredient can be applied to the prevention and treatment of metabolic disorders, including hyperlipidemia and arteriosclerosis, as well as obesity and diabetes.

The composition comprising the indole derivatives of Chemical Formula 1 as an active ingredient in accordance with the present invention can be administered either orally or non-orally, and may be provided in general medicine forms.

Dosage forms for oral administration of the compound of the present invention may be tablets, pills, soft/hard capsules, liquids, suspensions, emulsions, syrups, granules, elixirs, etc. The dosage forms comprise the active ingredient according to the present invention optionally in combination with a diluent (e.g., lactose, dextrose, sucrose, mannitol, sorbitol, cellulose and/or glycine), a lubricant (e.g., silica, talc, stearic acid or magnesium or calcium salts thereof, and/or polyethylene glycol). Besides, a binder, such as magnesium aluminum silicate, starch paste, gelatin, methylcellulose, sodium carboxymethyl cellulose, and/or polyvinylpyrrolidone, may also be added. Optionally, the oral dosage forms may include disintegrants, such as starch, agar, alginate or sodium salts thereof, boiling mixtures, colorants, flavors, and sweeteners, alone or in combination.

Also, the composition comprising the derivative of Chemical Formula 1 as an active ingredient may be in non-oral dosage forms suitable for subcutaneous injection, intramuscular injection or intrathoracic injection.

For non-oral dosage preparations, the indole derivatives of Chemical Formula 1 or the pharmaceutically acceptable salts thereof may be dissolved in combination with a stabilizer or a buffer in water to give a solution or suspension which is then packaged into ampoules or vials for unit injection. The solution may further comprise supplements, such as preservatives, stabilizers, hydrates, emulsifiers, salts for osmosis control, buffers, and other therapeutically useful materials. These materials can be formulated in combination with the active ingredient into desirable dosage forms according to typical methods, such as mixing, granulation or coating.

The indole derivatives of Chemical Formula 1 in accordance with the present invention may be administered via oral or non-oral routes in a single dose or in two or three doses per day, each dose ranging from 0.5 to 100 mg/kg of body weight.

MODE FOR INVENTION

A better understanding of the present invention may be obtained in light of the following examples which are set forth to illustrate, but are not to be construed to limit the present invention.

Example 1

Preparation of 3-(3-1H-indol-3-yl-propionylamino)-benzamide

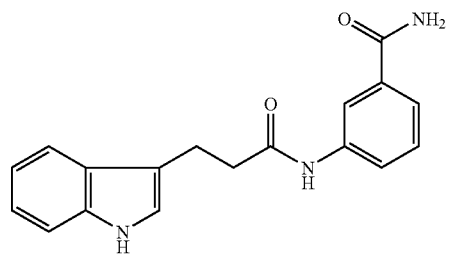

In 5.0 mL of dimethylformamide were dissolved 3-(1H-indol-3-yl)-propionic acid (189 mg, 1.0 mmol) and 3-aminobenzamide (68.1 mg, 0.5 mmol), followed by the addition of benzotriazol-1-yl-oxitripyrrolidino phosphonium hexafluorophosphate (520.3 g, 1.0 mmol) and N,N-diisopropylethyl amine (0.17 ml, 1.0 mmol). The resulting solution was stirred at room temperature and mixed with ethyl acetate and an aqueous sodium salt solution. The organic layer was dried over anhydrous magnesium sulfate, concentrated, and purified using silica gel column chromatography (n-hexane:ethyl acetate:methanol=6:3:1) to produce the subject compound 1 as a white solid (77.2 mg, 50%).

¹H-NMR (DMSO-d₆, 300 Hz): 8.02 (1H, s, Aromatic), 7.75 (1H, d, J=7.8 Hz, Aromatic), 7.50 (2H, m, Aromatic), 7.32 (2H, m, Aromatic), 6.93-7.09 (3H, m, Aromatic), 3.04 (2H, t, J=7.8 Hz, Aliphatic), 2.68 (2H, t, J=7.2 Hz, Aliphatic).

Example 2

Preparation of
3-(3-1H-indol-3-yl-acryloylamino)-benzamide

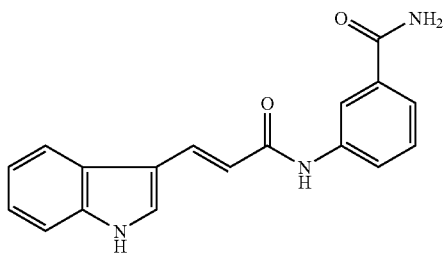

In 5.0 mL of dimethylformamide were dissolved 3-(1H-indol-3-yl)-acrylic acid (187 mg, 1.0 mmol) and 3-aminobenzamide (68.1 mg, 0.5 mmol), followed by the addition of benzotriazol-1-yl-oxitripyrrolidino phosphonium hexafluorophosphate (520.3 g, 1.0 mmol) and N,N-diisopropylethyl amine (0.17 ml, 1.0 mmol). The resulting solution was stirred at room temperature and mixed with ethyl acetate and an aqueous sodium salt solution. The organic layer was dried over anhydrous magnesium sulfate, concentrated, and purified using silica gel column chromatography (n-hexane:ethyl acetate:methanol=5:3:1) to produce the subject compound (2) as a yellow solid (34.3 mg, 23%).

¹H-NMR (CD₃OD, 300 Hz): 8.17 (1H, s, Aromatic), 7.83-7.97 (3H, m, Aromatic), 7.58 (2H, m, Aromatic), 7.41 (2H, m, Aromatic), 7.19 (2H, m, Aromatic), 6.77 (1H, d, J=15.9 Hz, Aromatic).

Example 3

Preparation of
3-(3-1H-indol-3-yl-propionylamino)-benzoic Acid Methyl Ester

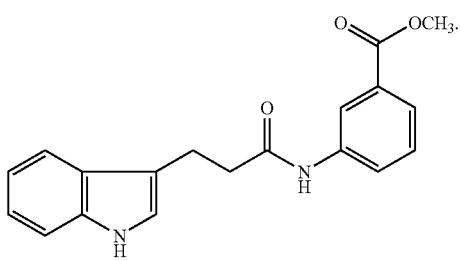

In 3.0 mL of dimethylformamide were dissolved 3-indole propionic acid (100 mg, 0.528 mmol), 3-amino benzoic acid methyl ester (119 mg, 0.792 mmol), and N,N-diisopropylethylamine (102 mg, 0.792 mmol), followed by the addition of ethylenedichloride (151 mg, 0.792 mmol) and N-hydroxybenzotriazole (107 mg, 0.792 mmol) at room temperature. The resulting solution was stirred at room temperature before being mixed with 100 ml of water. The precipitate thus formed was extracted with ethyl acetate and washed with an aqueous sodium chloride solution, 5% citric acid and water. The organic layer thus formed was dried over anhydrous magnesium sulfate, filtered, and concentrated. The residue was purified using silica gel column chromatography (ethyl acetate:n-hexane=1:9~4:6) to yield the subject compound (3) as a colorless solid (0.16 g, 94%).

¹H NMR (CDCl₃, 300 MHz): 8.08 (1H, s, CONH), 7.88 (1H, s, indole NH), 7.73 (2H, d, J=7.2 Hz, Aromatic), 7.60 (1H, d, J=7.2 Hz, Aromatic), 7.39-7.09 (5H, m, indole), 6.97 (1H, d, J=1.8 Hz, Aromatic), 3.86 (3H, s, OCH₃), 3.18 (2H, t, J=7.35 Hz, CH₂CONH), 2.74 (2H, t, J=7.5 Hz, CH₂CH₂CONH).

Example 4

Preparation of
3-(3-1H-indol-3-yl-acryloylamino)-benzoic Acid Methyl Ester

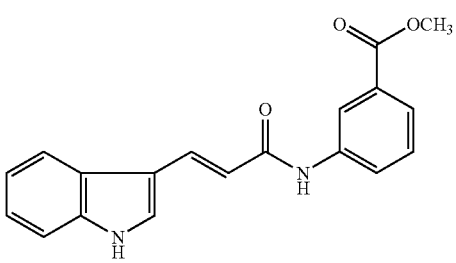

In 5.0 mL of dimethylformamide were dissolved 3-(1H-indol-3-yl)-acrylic acid (150 mg, 0.8 mmol) and 3-amino benzoic acid methyl ester (218 mg, 1.44 mmol), followed by the addition of ethylenedichloride (230 mg, 1.2 mmol), N-hydroxybenzotriazole (163 mg, 1.2 mmol), and N,N-diisopropylethylamine (0.21 ml, 1.2 mmol). The resulting solution was stirred at room temperature and mixed with ethyl acetate and an aqueous sodium salt solution. The organic layer was dried over anhydrous magnesium sulfate. After the filtration and concentration of the residue, the concentrate was purified using silica gel column chromatography (n-hexane:ethyl acetate methanol=9:3:1) to produce the subject compound (4) as a yellow solid (102 mg, 38%).

¹H-NMR (CDCl₃, 300 Hz): 8.90 (1H, s, NH), 8.21 (1H, s, NH), 7.86-8.03 (4H, m, aromatic), 7.76 (1H, d, J=8.1 Hz aromatic), 7.36-7.41 (3H, m, aromatic), 7.20 (2H, m, aromatic), 6.60 (2H, d, J=15.3 Hz, aromatic), 3.88 (3H, s, OCH₃).

Example 5

Preparation of
3-(3-1H-indol-3-yl-propionylamino)-benzoic Acid

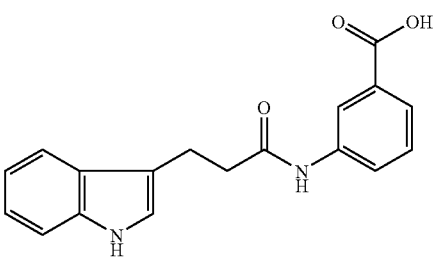

In a mixture of dioxane and water (7 ml:7 ml) was dissolved 3-(3-1H-indol-3-yl-propionylamino)-benzoic acid methyl ester (100 mg, 0.31 mmol), prepared in Example 3, followed by the addition of lithium hydroxide (39 mg, 0.93 mmol) at room temperature. Stirring was continued at 50° C. until the completion of reaction. After the removal of dioxane in a vacuum, the solution was cooled and neutralized to pH 7. The white precipitates thus separated were collected through filtration and purified through flash silica gel chromatography (ethyl acetate:n-hexane=1:9~1:1) to yield the subject compound (5) as a colorless solid (0.08 g, 80%).

$^1$H NMR (DMSO-$d_6$, 300 MHz): 10.79 (1H, s, CONH), 10.07 (1H, s, indole NH), 8.17 (1H, s, indole), 7.76 (1H, d, J=7.8 Hz, indole), 7.62-7.55 (2H, m, indole), 7.31 (2H, dd, J=3.15, 7.95 Hz, aromatic), 7.13 (1H, d, J=7.8 Hz, indole), 7.08-6.94 (2H, m, aromatic), 3.02 (2H, t, J=7.5 Hz, CH$_2$CONH), 3.02 (2H, t, J=7.5 Hz, CH$_2$CH$_2$CONH).

Example 6

Preparation of 3-(3-1H-indol-3-yl-acryloylamino)-benzoic Acid

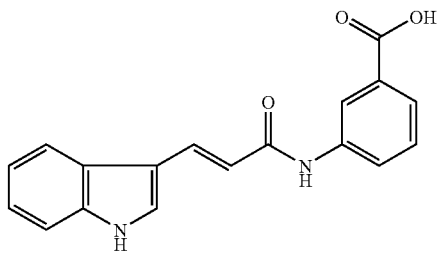

In a mixture of tetrahydrofuran and water (1:1, 10 mL) was dissolved 3-(3-1H-indol-3-yl-acryloylamino)-benzoic acid methyl ester (188 mg, 0.59 mmol), prepared in Example 4, followed by the addition of lithium hydroxide (49.3 mg, 1.17 mmol) at room temperature. Stirring was continued until the completion of reaction. The solution was acidified to pH 2 with 10% hydrochloric acid. An organic layer resulting from the addition of ethylacetate was removed, concentrated, and purified using silica gel column chromatography (methylene chloride:methanol=15:1) to yield the subject compound (6) as a white solid (98.5 mg, 55%).

$^1$H-NMR (CD$_3$OD, 300 Hz): 8.35 (1H, s, aromatic), 7.90-7.96 (3H, m, aromatic), 7.74 (1H, d, J=7.8 Hz, aromatic), 7.58 (1H, s, aromatic), 7.41 (2H, m, aromatic), 7.19 (2H, m, aromatic), 6.78 (1H, d, J=15 Hz aromatic).

Example 7

Preparation of 3-(3-1H-indol-3-yl-acryloylamino)-N-(2-piperidin-1-yl-ethyl)-benzamide

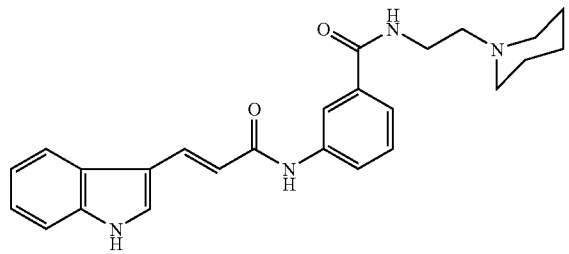

In 5.0 mL of dimethylformaide were dissolved 3-(3-1H-indol-3-yl-acryloylamino)-benzoic acid (150 mg, 0.49 mmol), prepared in Example 6, and 2-piperidin-1-yl-ethylamine (0.10 mL, 0.73 mmol), followed by the addition of O-(7-azabenzotriazol-1-yl)-N,N,N',N'-tetramethyl uronium hexafluorophosphate (277.6 mg, 0.73 mmol) and N,N-diisopropylethylamine (0.13 ml, 0.73 mmol). The resulting solution was stirred at room temperature and mixed with ethyl acetate and an aqueous sodium salt solution. The organic layer was dried over anhydrous magnesium sulfate. After the filtration and concentration of the residue, the concentrate was purified using Prep-TLC (methylene chloride:methanol=10:1) to produce the subject compound (7) as a yellow solid (71:1 mg, 35%).

$^1$H-NMR (DMSO-$d_6$, 300 Hz): 11.67 (1H, brs, aromatic), 10.16 (1H, s, aromatic), 8.41 (1H, s, aromatic), 8.11 (1H, s, aromatic), 7.76-7.98 (4H, m, aromatic), 7.38-7.50 (3H, m, aromatic), 7.23 (2H, m, aromatic), 6.84 (1H, d, J=15.9 Hz, aromatic) 3.33-3.43 (6H, m, aliphatic), 2.51 (2H, m, aliphatic), 1.41-1.54 (6H, m, aliphatic).

Example 8

Preparation of 3-(3-1H-indol-3-yl-acryloylamino)-N-(3-morpholin-4-yl-propyl)-benzamide

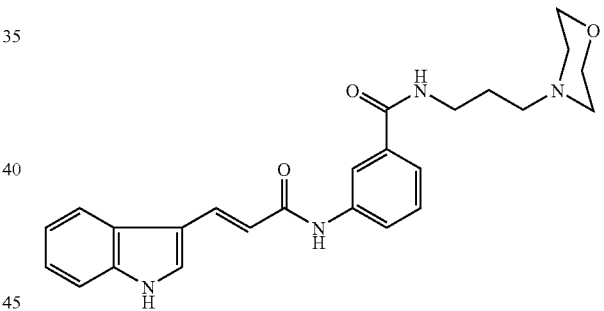

In 5.0 mL of dimethylformamide were dissolved 3-(3-1H-indol-3-yl-acryloylamino)-benzoic acid (150 mg, 0.49 mmol), prepared in Example 3, and 3-morpholin-4-yl-propylamine (0.11 mL, 0.73 mmol), followed by the addition of O-(7-azabenzotriazol-1-yl)-N,N,N',N'-tetramethyl uronium hexafluorophosphate (277.6 mg, 0.73 mmol) and N,N-diisopropylethylamine (0.13 ml, 0.73 mmol). The resulting solution was stirred at room temperature and mixed with ethyl acetate and an aqueous sodium salt solution. The organic layer was dried over anhydrous magnesium sulfate. After the filtration and concentration of the residue, the concentrate was purified using Prep-TLC (methylene chloride:methanol=10:1) to produce the subject compound as a yellow solid (8) (92.6 mg, 44%).

$^1$H-NMR (DMSO-$d_6$, 300 Hz): 11.66 (1H, brs, aromatic), 10.14 (1H, s, aromatic), 8.46 (1H, ps t, J=5.4 Hz, aromatic), 8.09 (1H, s, aromatic), 7.76-7.98 (4H, m, aromatic), 7.37-7.50 (3H, m, aromatic), 7.22 (2H, m, aromatic), 6.82 (1H, d, J=15.9 Hz, aromatic), 3.55-3.59 (4H, m, aliphatic), 3.27 (1H, m, aliphatic), 3.16 (1H, d, J=15.9 Hz, aliphatic), 2.31-2.36 (6H, m, aliphatic) 1.69 (2H, m, aliphatic).

Example 9

Preparation of N-furan-2-ylmethyl-3-(3-1H-indol-3-yl-acryloylamino)-benzamide

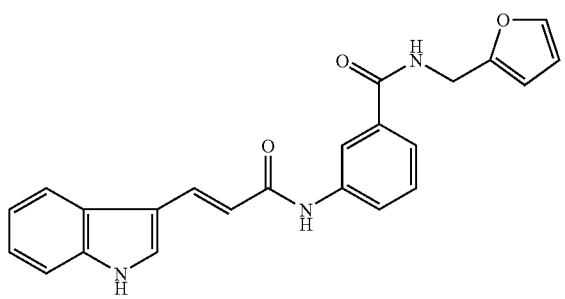

In TFA/methylene chloride (1:3, 2 mL) was dissolved 3-(2-3-[(furan-2-ylmethyl)-carbamoyl]-phenylcarbamoyl-vinyl)-indole-1-carboxylic acid-t-butyl ester (25.3 mg, 0.052 mmol) at room temperature with stirring. After the removal of the solvent and trifluoroacetic acid in a vacuum, the brown solid thus formed was dissolved in an aqueous sodium hydrogen carbonate and extracted with ethyl acetate. The organic layer was collected and concentrated. The concentrate was purified using Prep-TLC (methylene chloride:methanol=20:1) to yield the subject compound (9) as a yellow solid (8.8 mg, 44%).

$^1$H-NMR (CD$_3$OD, 300 Hz): 8.13 (1H, m, aromatic), 7.96 (2H, m, aromatic), 7.82 (1H, m, aromatic), 7.63 (1H, s, aromatic), 7.52 (1H, m, aromatic), 7.39-7.45 (3H, m, aromatic), 7.20 (2H, m, aromatic), 6.78 (1H, d, J=15.9 Hz, aromatic), 6.32 (2H, m, aromatic), 4.56 (2H, s, NHCH$_2$).

Example 10

Preparation of 3-(2-3-[(Furan-2-ylMethyl)-Carbamoyl]-Phenylcarbamoyl-Vinyl)-Indole-1-Carboxylic Acid-t-Butyl Ester

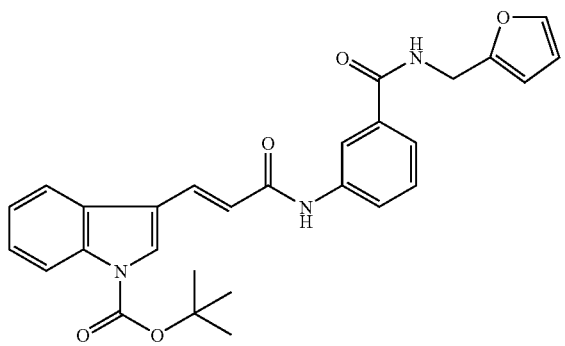

N-furan-2-ylmethyl-3-(3-1H-indol-3-yl-acryloylamino)-benzamide (62.4 mg, 0.16 mmol), prepared in Example 9, was dissolved, together with anhydrous sodium carbonate (88.4 mg, 0.64 mmol), in 3 ml of tetrahydrofuran, and di-t-butoxydicarbonate (0.06 ml, 0.24 mmol) was added dropwise to the solution at 0° C. before stirring for 12 hours. The reaction mixture was diluted with EtOAc and washed with brine and water, followed by purification through silica gel column chromatography (methylene chloride:methanol=20:1) to yield the subject compound (10) as a yellow solid (29.0 mg, 81%).

$^1$H-NMR (CD$_3$OD, 300 Hz): 8.12 (2H, m, aromatic), 7.92 (2H, m, aromatic), 7.78 (2H, m, aromatic), 7.52 (1H, d, J=7.8 Hz, aromatic), 7.30-7.43 (5H, m, aromatic), 6.90 (1H, d, J=15.9 Hz, aromatic), 6.32 (2H, m, aromatic), 4.55 (2H, s, NHCH$_2$), 1.68 (9H, s, (CH$_3$)$_3$).

Example 11

Preparation of 3-[3-(1-Benzyl-1H-indol-3-yl)-acryloylamino]-N-furan-2-ylmethyl-benzamide

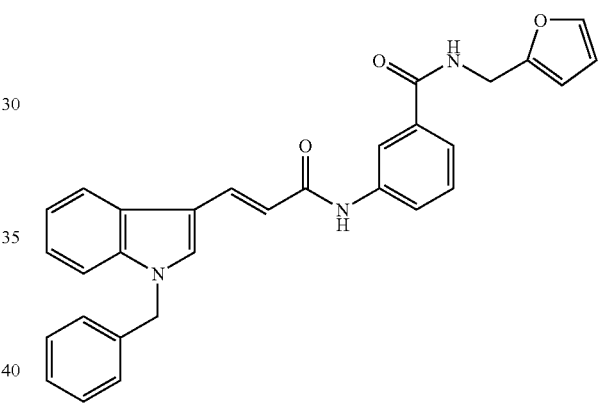

N-furan-2-ylmethyl-3-(3-1H-indol-3-yl-acryloylamino)-benzamide (62.4 mg, 0.16 mmol), prepared in Example 9, was dissolved, together with anhydrous sodium carbonate (33.6 mg, 0.24 mmol), in dimethylformamide (3 mL), and benzylbromide (41.6 mg, 0.03 mL, 0.24 mmol) was added dropwise to the solution at room temperature before stirring for 12 hours. The reaction mixture was diluted with ethyl acetate and washed with brine and water. The organic layer was dried over anhydrous magnesium sulfate, filtered and concentrated. The concentrate was purified using Prep-TLC (methylene chloride:methanol=30:1) to yield the subject compound (11) as a yellow solid (5.2 mg, 6.8%).

$^1$H-NMR (CD$_3$OD+CDCL$_3$, 300 Hz): 7.94, 7.86 (2H, m, aromatic), 7.87 (1H, d, J=15.9 Hz, aromatic), 7.74 (1H, d, J=9.3 Hz, aromatic), 7.10-7.53 (12H, m, aromatic), 6.71 (1H, d, J=15.3 Hz, aromatic), 6.25 6.30 (2H, m, aromatic), 5.31 (2H, s, CHA, 4.55 (2H, s, CHA; and MS (ESI) m/z: 598 (M$^+$+Na), 474 (M−H).

Example 12

Preparation of 3-{3[1-(2-Dimethylamino-ethyl)-1H-indol-3-yl]-acryloylamino}-N-furan-2-ylmethyl-benzamide

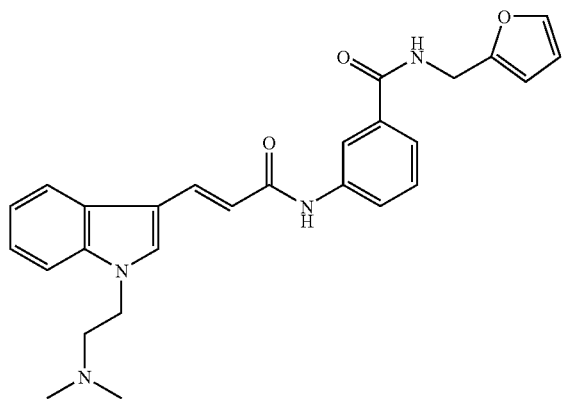

N-furan-2-ylmethyl-3-(3-1H-indol-3-yl-acryloylamino)-benzamide (51.7 mg, 0.13 mmol), prepared in Example 9, was dissolved in dimethylformamide (3 mL), and 2-dimethylaminoethyl chloride (38.9 mg, 0.27 mmol) was added dropwise to the solution at 50° C. before stirring for 12 hours. The reaction mixture was diluted with ethyl acetate and washed with brine and water. The organic layer was dried over anhydrous magnesium sulfate, filtered and concentrated. The concentrate was purified using Prep-TLC (n-hexane:ethyl acetate:methanol=6:3:1) to yield the subject compound (12) as a yellow solid (5.3 mg, 8.7%).

$^1$H-NMR (CD$_3$OD, 300 Hz): 8.12 (1H, m, aromatic), 7.97 (1H, d, J=7.5 Hz, aromatic), 7.89 (1H, d, J=15.3 Hz, aromatic), 7.81 7.84 (1H, m, aromatic), 7.69 (1H, s, aromatic), 7.39 7.54 (4H, m, aromatic), 7.19-7.32 (2H, m, aromatic), 6.77 (1H, d, J=15.9 Hz, aromatic), 6.30 6.37 (2H, m, aromatic), 4.56 (2H, s, CH$_2$), 4.35 (2H, t, J=6.6 Hz, CH$_2$), 2.80 (2H, t, J=6.9 Hz, CH$_2$), 2.32 (6H, s, CH$_3$); and MS (ESI) m/z: 557 (M$^+$+H), 455 (M−H).

Example 13

Preparation of [3-(2-{3-[(Furan-2-ylmethyl)-carbamoyl]-phenylcarbamoyl}-vinyl)-indol-1-yl]-acetic acid-t-butyl Ester

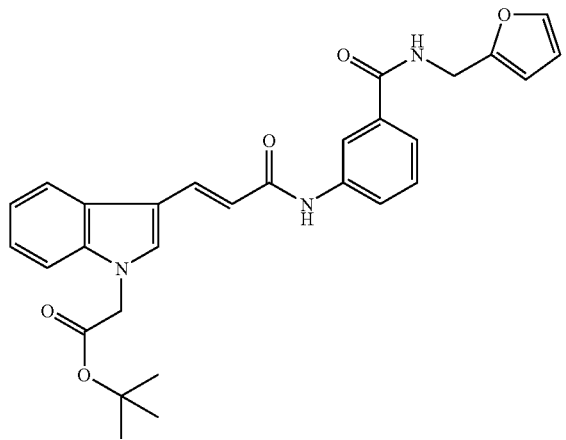

N-furan-2-ylmethyl-3-(3-1H-indol-3-yl-acryloylamino)-benzamide (60.1 mg, 0.16 mmol), prepared in Example 9, was dissolved, together with anhydrous sodium carbonate (33.2 mg, 0.24 mmol), in dimethylformamide (4 mL), and t-butylbromoacetate (46.8 mg, 0.04 ml, 0.24 mmol) was added dropwise to the solution at 50° C. before stirring for 12 hours. The reaction mixture was diluted with ethyl acetate and washed with brine and water. The organic layer was dried over anhydrous magnesium sulfate, filtered and concentrated. The concentrate was purified using Prep-TLC (n-hexane:ethylacetate:methanol=6:3:1) to yield the subject compound (13) as a yellow solid (27.4 mg, 34.3%).

$^1$H-NMR (CD$_3$OD, 300 Hz): 8.12 (1H, m, aromatic), 7.94 (1H, m, aromatic), 7.79 7.89 (2H, m, aromatic), 7.20-7.56 (7H, m, aromatic), 6.77 (1H, d, J=15.9 Hz, aromatic), 6.29 6.36 (2H, m, aromatic), 4.90 (2H, s, CH$_2$), 4.55 (2H, s, CH$_2$), 1.43 (9H, s, CH$_3$); and MS (ESI) m/z: 522 (M$^+$+Na), 498 (M−H).

Example 14

Preparation of N-furan-2-ylmethyl-3-[(3-(1-phenyl-methanesulfonyl-1H-indol-3-yl)-acryloylamino]-benzamide

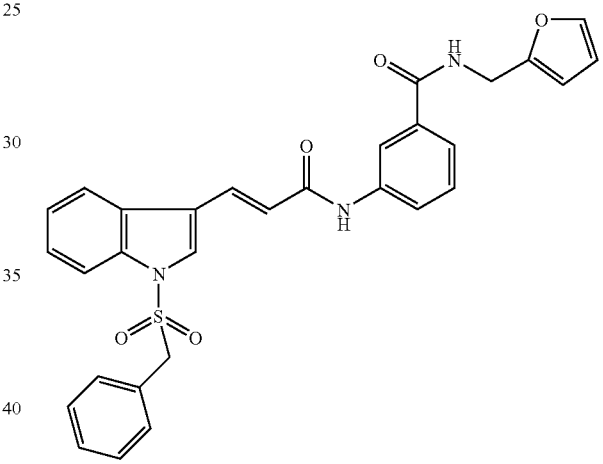

Sodium hydride (6.4 mg, 0.12 mmol) was added to anhydrous dimethylformamide (2.5 ml) with stirring at 0° C. for 10 min. To this mixture was added dropwise a solution of N-furan-2-ylmethyl-3-(3-1H-indol-3-yl-acryloylamino)-benzamide (60.1 mg, 0.16 mmol), prepared in Example 9, in anhdrous dimethylformamide (1.5 ml) under an argon atmosphere with stirring at room temperature for 1 hour and the reaction mixture was cooled to 0° C. A solution of benzylsulfonyl chloride in anhydrous dimethylformamide (1.5 ml) was added and then stirred at room temperature for 12 hours. The resulting reaction mixture was diluted with ethyl acetate and washed with brine and water. The organic layer was dried over anhydrous magnesium sulfate, filtered and concentrated. The concentrate was purified using Prep-TLC (n-hexane:ethylacetate:methanol=6:3:1) to yield the subject compound (14) as a yellow solid (23.3 mg, 36.0%).

$^1$H-NMR (CD$_3$OD, 300 Hz): 8.12 (1H, m, aromatic), 7.95 (1H, d, J=7.2 Hz, aromatic), 7.75-7.84 (2H, m, aromatic), 7.67 (1H, d, J=15.9 Hz, aromatic), 7.54 (1H, d, J=7.8 Hz, aromatic), 7.31-7.44 (5H, m, aromatic), 7.21-7.26 (1H, m, aromatic), 7.12 (2H, ps-t, J=7.2 Hz, aromatic), 6.90 (1H, d, J=9 Hz, aromatic), 6.30-6.36 (2H, m, aromatic), 4.78 (2H, s, CH$_2$), 4.56 (2H, s, CH$_2$); and MS (ESI) m/z: 562 (M$^+$+Na), 538 (M−H).

Example 15

Preparation of N-furan-2-ylmethyl-3-[3-[1-(thiophene-2-sulfonyl)-1H-indol-3-yl]-acryloylamino]-benzamide

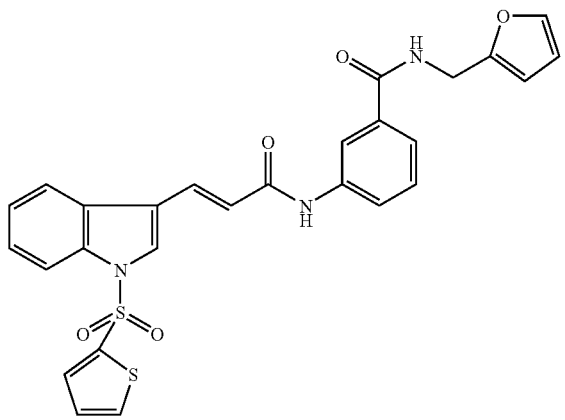

t-Butoxy potassium (106.6 mg, 0.95 mmol) was added to a solution of N-furan-2-ylmethyl-3-(3-1H-indol-3-yl-acryloylamino)-benzamide (120.1 mg, 0.31 mmol), prepared in Example 9, in anhydrous dimethylformamide (4 ml) under an argon atmosphere and stirred at room temperature for 1 hour. To this reaction mixture was added 2-thiophenesulfonyl chloride (85.8 mg, 0.47 mmol) and stirring was carried out at room temperature for 12 hours. The resulting solution was diluted with ethylacetate and washed with brine and water. The organic layer was dried over anhydrous magnesium sulfate, filtered and concentrated. The concentrate was purified using Prep-TLC (n-hexane:ethyl acetate:methanol=6:3:1) to yield the subject compound (15) as a yellow solid (40.4 mg, 24.5%).

$^1$H-NMR (CD$_3$OD, 300 Hz): 8.13 (1H, m, aromatic), 8.05 (2H, d, J=6.6 Hz, aromatic), 7.95 (1H, d, J=7.2 Hz, aromatic), 7.79-7.87 (4H, m, aromatic), 7.55 (1H, d, J=8.1 Hz, aromatic), 7.37-7.47 (4H, m, aromatic), 7.08-7.11 (1H, m, aromatic), 6.95 (1H, d, J=15.9 Hz, aromatic), 6.30-6.37 (2H, m, aromatic), 4.56 (2H, s, CH$_2$); and MS (ESI) m/z: 554 (M$^+$+Na), 530 (M−H).

Example 16

Preparation of 3-[3-(1-Acetyl-1H-indol-3-yl)-acryloylamino]-N-furan-2-ylmethyl-benzamide

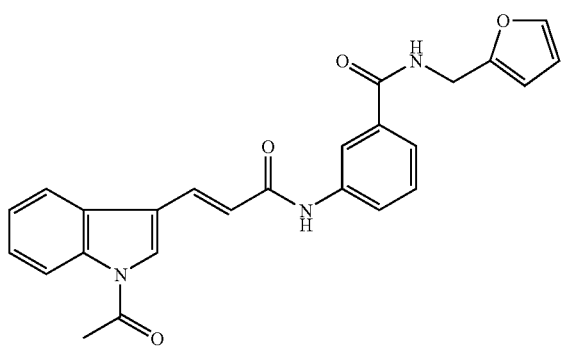

N-furan-2-ylmethyl-3-(3-1H-indol-3-yl-acryloylamino)-benzamide (60.4 mg, 0.16 mmol), prepared in Example 9, was dissolved, along with anhydrous potassium carbonate (660.5 mg, 0.48 mmol) and dimethylaminophaphate (2.4 mg, 0.02 mmol), in DMF (3 ml). Acetic anhydride (32.7 mg, 0.03 mL, 0.32 mmol) was added dropwise at room temperature to the solution which was then stirred for 12 hours. The resulting reaction mixture was diluted with ethyl acetate and washed with brine and water. The organic layer was dried over anhydrous magnesium sulfate, filtered and concentrated. The concentrate was purified using Prep-TLC (methylene chloride:methanol=30:1) to yield the subject compound (16) as a yellow solid (35.2 mg, 54.7%).

$^1$H-NMR (CD$_3$OD, 300 Hz): 8.45 8.48 (1H, m, aromatic), 8.10 8.14 (2H, m, aromatic), 7.96 7.99 (1H, m, aromatic), 7.82-7.88 (2H, m, aromatic), 7.55 (1H, d, J=8.1 Hz, aromatic), 7.37 7.46 (4H, m, aromatic), 6.98 (1H, d, J=15.9 Hz, aromatic), 6.30 6.37 (2H, m, aromatic), 4.56 (2H, s, CH$_2$), 2.69 (3H, s, CH$_3$); and MS (ESI) m/z: 450 (M$^+$+Na), 426 (M−H).

Formulation Example 1

Preparation of Powder

| | |
|---|---|
| Indole derivative of Chemical Formula 1 | 2 g |
| Lactose | 1 g |

The above ingredients were mixed and loaded into an airtight sac to produce powder.

Formulation Example 2

Preparation of Tablet

| | |
|---|---|
| Indole derivative of Chemical Formula 1 | 100 mg |
| Corn Starch | 100 mg |
| Lactose | 100 mg |
| Mg Stearate | 2 mg |

These ingredients were mixed and prepared into tablets using a typical tabletting method.

Formulation Example 3

Preparation of Capsule

| | |
|---|---|
| Indole derivative of Chemical Formula 1 | 100 mg |
| Corn Starch | 100 mg |
| Lactose | 100 mg |
| Mg Stearate | 2 mg |

These ingredients were mixed and loaded into gelatin capsules according to a typical method to produce capsules.

Experimental Example 1

Assay for Inhibitory Activity Against DGAT

The following experiment was performed in order to examine the inhibitory activity of the indole derivatives of the present invention against DGAT. After enzymatic reaction between two substrates, 1,2-diacylglycerol (Sigma, D0138) and [$^{14}$C]palmitoyl-CoA (Amersham, CFA583), with the microsomal protein of rats serving as an enzyme source in accordance with Coleman et al, *Methods Enzymol.*, 98-103, 1992, the resulting product [$^{14}$C] triacylglycerol was measured for radioactivity.

In detail, to a reaction buffer (175 mM Tris-HCl, pH 8.0, 20 μl bovine serum albumin (10 mg/ml), 100 mM MgCl$_2$, 30 μM [$^{14}$C] palmitoyl-CoA (0.02 μCi, Amersham) and 200 μM 1,2-dioleoyl glycerol) was added 10 μl of a solution of the samples in dimethylsulfoxide (DMSO) and then 100-200 μl of an isolated microsomal protein, followed by reaction at 25° C. for 10 min. The reaction was terminated with 1.5 ml of a mixture of 80:20:2 2-propanol:heptane:water (v:v:v). Thereafter, the [$^{14}$C] triacylglycerol thus formed was separated. In this regard, 1 ml of heptane and 0.5 ml of distilled water were added to the reaction mixture, which was then shaken. 1 ml of the supernatant thus formed was mixed with 2 ml of an alkaline ethanol solution (ethanol:0.5 N sodium hydroxide:water=50:10:40, v:v:v), followed by shaking. After it was recovered, 0.65 ml of the supernatant thus formed was measured for radioactivity using an LSC (liquid scintillation counter). The inhibitory activity against DGAT was calculated according to the following Mathematical Formula 1. The inhibitory effects of the indole derivatives on DGAT are summarized in Table 2, below.

$$\% \text{ Inhibition} = \left(1 - \frac{T-B}{C-B}\right) \times 100 \quad \text{[Mathematical Formula 1]}$$

T: Cpm of a test group in which a sample was added to an enzymatic buffer,

C: Cpm of a control in which no samples were added to an enzymatic buffer,

B: Cpm of a control in which a sample was added in the absence of any enzyme source.

TABLE 2

| Cpd. | DGAT (inhibition % in 5 μM) | DGAT (inhibition % in 25 μM) |
|---|---|---|
| 1 | — | 4.66 |
| 2 | — | 19.36 |
| 3 | — | — |
| 4 | — | 18.72 |
| 5 | — | 0.08 |
| 6 | — | 11.52 |
| 7 | −5.29 | −3.11 |
| 8 | 3.06 | 2.05 |
| 9 | 2.72 | 13.24 |
| 10 | 60.22 | 78.68 |
| 11 | 54.09 | 64.13 |
| 12 | −11.04 | −0.38 |
| 13 | −0.95 | 53.15 |
| 14 | 43.19 | 50.89 |
| 15 | 40.88 | 49.88 |
| 16 | −10.09 | 39.82 |

As shown in Table 2, Compounds 10, 11, 14 and 15 were found to have potent inhibitory activity against DGAT in a dose-dependent manner when they were used in the presence of rat hepatic microsomal protein as an enzyme source, with 1,2-diacylglycerol and [$^{14}$C] palmitoyl-CoA serving as substrates.

Experimental Example 2

Assay for Inhibitory Effect on DGAT in Cell

The effect of the indole derivatives of the present invention on DGAT was examined with HepG2 cells, hepatic cells derived from the human liver, as follows.

HepG2 cells, purchased from ATCC, were cultured in MEM (Minimum Essential Medium, 2 mM L-glutamine, Earle's BSS adjusted to contain 1.5 g/L sodium bicarbonate, 0.1 mM nonessential amino acids, and 1 mM sodium pyruvate), supplemented with 10% fetal bovine serum (FBS) and 1% antibiotics (100 U/ml penicillin and 100 g/ml streptomycin) at 37° C. in a 5% CO$_2$ incubator.

Intracellular DGAT activity was represented by the amount of triglycerides produced in the cultured HepG2 cells while the compounds (1, 6, 10, 11 and 15) of Chemical Formula 1 were assayed for inhibitory activity against DGAT by measuring the change in intracellular triglyceride production after the addition thereof.

Cells were plated at a density of 1×10$^6$ cell/ml per well into 24-well plates and incubated for 24 hours. Then, the medium was exchanged with FBS-free MEM. Thereafter, 0.2 mCi of [$^{14}$C]acetate (Amersham) was added as a substrate to the cells, followed by incubation for 18 hours. The production of triglycerides was catalyzed by DGAT so that DGAT activity was determined by the amount of the triglyceride product, which could be measured using radioactivity. For use, the samples were dissolved in dimethyl sulfoxide (DMSO). In a control, triglycerides were synthesized using DMSO without any sample, with the production yield thereof taken as 100.

The amount of the triglyceride products synthesized was determined as follows. After completion of synthesis, the cells were suspended in PBS (phosphate-buffer-saline) to remove the substrate [$^{14}$C] acetate that was not absorbed into the cells or that did not react, and total lipids, including triglycerides, were extracted twice for 30 min with 0.5 ml of an extraction solvent mixture (hexane:isopropanol=3:2, v:v). 1 ml of the extract was concentrated with nitrogen gas. The total lipid residue thus formed was dissolved in an organic solvent mixture (chloroform:methanol=2:1) and loaded dropwise onto a thin layer chromatography plate (TLC; silica gel 60F254, 0.5 mm, Merck) using a mixture of 80:20:1 hexane:diethylether:acetic acid (v:v:v) as a developing solvent. After the separation of triglycerides (Rf value: 0.4) on TLC, the plate was brought into contact with an autoradiographic film for three hours, followed by image analysis (BAS-1500, Fuji Photo Film Co. Ltd.) to determine the [$^{14}$C] radioactivity of the triglycerides. The cells left after the extraction were suspended in 0.3 ml of a 0.1 N sodium hydroxide solution to measure the cellular protein concentration thereof.

The empirical values were obtained by dividing triglyceride radioactivity by protein level, with correction for experimental errors between test groups. The inhibitory activities of the compounds according to the present invention against DGAT in vivo are summarized in Table 3, below.

TABLE 3

| Cpd. (10 μM) | Production Yield of Triglyceride (%) |
|---|---|
| 1 | 95.5 ± 5.7 |
| 6 | 92.5 ± 6.7 |
| 10 | 49.2 ± 5.7 |
| 11 | 55.5 ± 7.2 |
| 15 | 61.5 ± 7.1 |

As is apparent from the data of Table 3, the HepG2 cells treated with 10 μM of the compounds (1, 6, 10, 11 and 15) produced smaller amounts of triglycerides than did the control. Particularly, Compounds 10, 11 and 15 were measured to inhibit the biosynthesis of triglycerides by 50.8%, 44.5%, and 38.5%, respectively.

It is also speculated that the inhibition of these compounds occurs within the cells as they enter the cells.

Experimental Example 3

Assay of Indole Derivatives for Acute Toxicity

An assay of the indole derivatives in accordance with the present invention was performed to determine acute toxicity on mice (20±5 g, Central Lab. Animal Inc.) and rats (235±10 g, Central Lab. Animal Inc.).

For this, ICR mice and Sprague-Dawley rats were assigned to 4 groups of 10 and orally administered with Compound 22 in doses of 100 and 250 mg/kg for two weeks. Death was observed in none of the four groups, with no apparent symptoms different from the control.

In addition, the compounds of the present invention were orally administered once at a dose of as high as 2,000 mg/kg into mice. In this regard, 7-week-old male SPF ICR mice (Dae Han Biolink Co. Ltd.) were acclimated to a new environment for one week and then, at 8 weeks of age, were divided into two groups of three. The test group was orally administered once with a dose of 2 g/kg of Compound 10 in a 0.5% CMC solution, while the control was administered with a 0.5% CMC (carboxymethyl cellulose) solution alone. They were monitored for death, clinical signs, change in body weight and the like for a couple of weeks. Autopsies were performed to examine the abnormality of organs. The observations are given in Table 4, below.

TABLE 4

| Groups | Mortality | Clinical Signs | Necropsy Findings | Body Weight (g) | | | | |
|---|---|---|---|---|---|---|---|---|
| | | | | Day 0 | Day 1 | Day 3 | Day 7 | Day 14 |
| Test | 0/3 | ND | ND | 36 ± 0.5 | 38 ± 1.0 | 38 ± 0.2 | 39 ± 1.2 | 42 ± 2.0 |
| Control | 0/3 | ND | ND | 33 ± 0.9 | 34 ± 1.2 | 35 ± 1.9 | 36 ± 1.2 | 39 ± 2.1 |

Mortality: No. of Dead/No of Tested
Body Weight: Mean ± SD
ND: Not detected

As seen in Table 4, death was observed in neither of the groups, with no animals observed to behave abnormally or show evidence of toxicity. In addition, both groups were observed to increase in body weight. Upon necropsy, no abnormalities were observed in any thoracic or abdominal organs.

Therefore, Compound 10 of the present invention exerts no oral acute toxicity on mice even when administered once at a dose of up to 2,000 mg/kg.

The invention claimed is:

1. An indole derivative represented by the following Chemical Formula 1 or a pharmaceutically acceptable salt thereof:

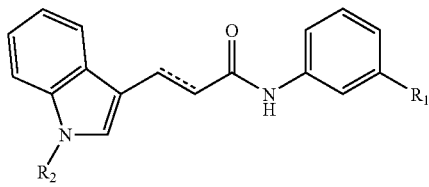

<Chemical Formula 1> wherein,
$R_1$ is one selected from a group consisting of $COOR_a$, $CONR_bR_c$ and $C_1$~$C_4$ alkyl,
wherein $R_a$ is H or $C_1$~$C_4$ alkyl, and
$R_b$ and $R_c$ are independently selected from a group consisting of $C_1$~$C_5$ alkyl bearing a 5-7 atom-membered heteroalkyl group containing N, O or S or a 5-7 atom-membered heterocyclic group containing N, O or S; H; and $C_1$~$C_5$ alkyl;
$R_2$ is selected from a group consisting of $C_5$~$C_7$ aryl $C_1$~$C_5$ alkyl, di-$C_1$~$C_5$ alkylamino $C_1$~$C_5$ alkyl, $C_1$~$C_5$ alkylcarbonyl, $C_1$~$C_5$ alkyl $C_1$~$C_5$ alkoxycarbonyl, $C_5$~$C_7$ aryl $C_1$~$C_5$ alkylsulfonyl, and thiophene $C_1$~$C_5$ alkylsulfonyl; and
the symbol ⁓ designates a single bond or a double bond.

2. The indole derivative or pharmaceutically acceptable salt thereof according to claim 1, wherein $R_1$ is selected from a group consisting of aminocarbonyl; methoxycarbonyl; hydroxycarbonyl; 2-piperidin-1-yl-ethylaminocarbonyl; 3-morpholin-4-yl-propylaminocarbonyl; and furan-2-yl-methylaminocarbony.

3. The indole derivative or pharmaceutically acceptable salt thereof according to claim 1, wherein $R_2$ is selected from a group consisting of H; butoxycarbonyl; benzyl; N,N-dimethyl-2-aminoethyl; acetyl; thiophene-2-sulfonyl; phenyl-methanesulfonyl; and t-butoxycarbonylmethyl.

4. The indole derivative or pharmaceutically acceptable salt thereof according to claim 1, wherein the indole derivative is selected from a group consisting of:
1) 3-(3-1H-indol-3-yl-propionylamino)-benzamide;
2) 3-(3-1H-indol-3-yl-acryloylamino)-benzamide;
3) 3-(3-1H-indol-3-yl-propionylamino)-benzoic acid methyl ester;
4) 3-(3-1H-indol-3-yl-acryloylamino)-benzoic acid methyl ester;
5) 3-(3-1H-indol-3-yl-propionylamino)-benzoic acid;
6) 3-(3-1H-indol-3-yl-acryloylamino)-benzoic acid;
7) 3-(3-1H-indol-3-yl-acryloylamino)-N-(2-piperidin-1-yl-ethyl)-benzamide;
8) 3-(3-1H-indol-3-yl-acryloylamino)-N-(3-morpholin-4-yl-propyl)-benzamide;
9) N-furan-2-ylmethyl-3-(3-1H-indol-3-yl-acryloylamino)-benzamide;
10) 3-(2-3-[(furan-2-ylmethyl)-carbamoyl]-phenylcarbamoyl-vinyl)-indole-1-carboxylic acid t-butyl ester;

11) 3-[3-(1-benzyl-1H-indol-3-yl)-acryloylamino]-N-furan-2-ylmethyl-benzamide;
12) 3-{3[1-(2-dimethylamino-ethyl)-1H-indol-3-yl]-acryloylamino}-N-furan-2-ylmethyl-benzamide;
13) [3-(2-{3-[(furan-2-ylmethyl)-carbamoyl]-phenylcarbamoyl}-vinyl)-indol-1-yl]-acetic acid t-butyl ester;
14) N-furan-2-ylmethyl-3-[3-(1-phenylmethanesulfonyl-1H-indol-3-yl)-acryloylamino]-benzamide;
15) N-furan-2-ylmethyl-3-{3-[1-(thiophene-2-sulfonyl)-1H-indol-3-yl]-acryloylamino}-benzamide; and
16) 3-[3-(1-acetyl-1H-indol-3-yl)-acryloylamino]-N-furan-2-ylmethyl-benzamide.

5. A method for preparing the indole derivative of claim 1, as elucidated in the following Reaction Scheme 1, comprising a condensation reaction between a starting material 3-(1H-indol-3-yl)propionic acid of Chemical Formula 2 and an amine derivative bearing an $R_1$ substituent of Chemical Formula 3 at room temperature in an organic solvent with the aid of a condensing agent in the presence of a base to produce a compound of Chemical Formula 1a

[Reaction Scheme 1]

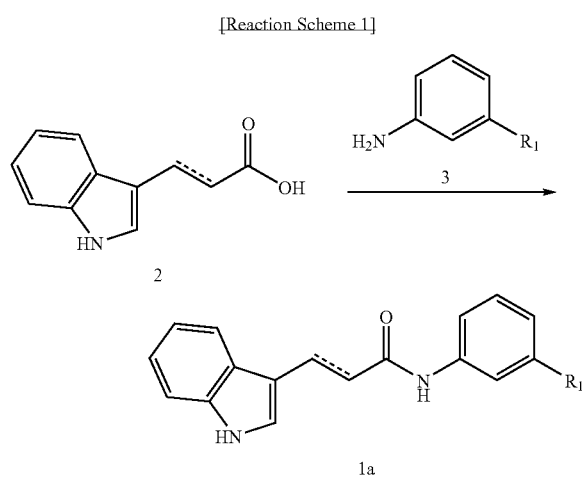

(wherein, $R_1$ is as defined in Chemical Formula 1, and the compound of Chemical formula 1a is included in the indole derivatives of Chemical Formula 1).

6. The method according to claim 5, wherein the amine derivative of chemical formula 3 is 3-amino-benzamide or 3-amino-benzoic acid methyl ester, the organic solvent is dimethylformamide or methylene chloride, the base is diisopropylamine or triethylamine, and the condensing reagent is selected from a group consisting of benzotriazol-1-yl-oxytripyrrolidino-phosphonium hexafluorophosphate (PyBOP), ethylene dichloride (EDC), N-hydroxybenzotriazole (HOBt), O-(benzotriazol-1-yl)-1,1,3,3-tetramethyl uronium hexafluorophosphate (HBTU) and O-(7-azabenzotriazol-1-yl)-N,N,N',N'-tetramethyl uronium hexafluorophosphate (HATU).

7. A method for preparing the indole derivative of claim 1, as elucidated in the following Reaction Scheme 2 when $R_1$ is —$COOR_a$, comprising:
condensing a starting material 3-(1H-indol-3-yl)propionic acid of Chemical Formula 2 with an amine derivative bearing —$COOR_a$ as $R_1$ of Chemical Formula 4 at room temperature in the presence of a base and a condensing reagent in an organic solvent to produce a derivative of Chemical Formula 1b in which the propionic acid and the amine derivative are coupled via an amide bond (Step 1);

de-esterifying the derivative of Chemical Formula 1b into a derivative of Chemical Formula 1c at room temperature in the presence of a base in an organic solvent/water mixture (Step 2);
condensing the derivative of Chemical Formula 1c with alkyl amine ($HNR_bR_c$) at room temperature or flux under the same conditions as in Step 1, including the solvent, the base and the condensing reagent to produce a derivative of Chemical Formula 1d in which the two reactants are coupled via an amide bond (Step 3); and
introducing $R_2$ onto the nitrogen atom of the derivative of Chemical Formula 1d in the presence of a base in an organic solvent to produce a derivative of Chemical Formula 1e (Step 4)

[Reaction Scheme 2]

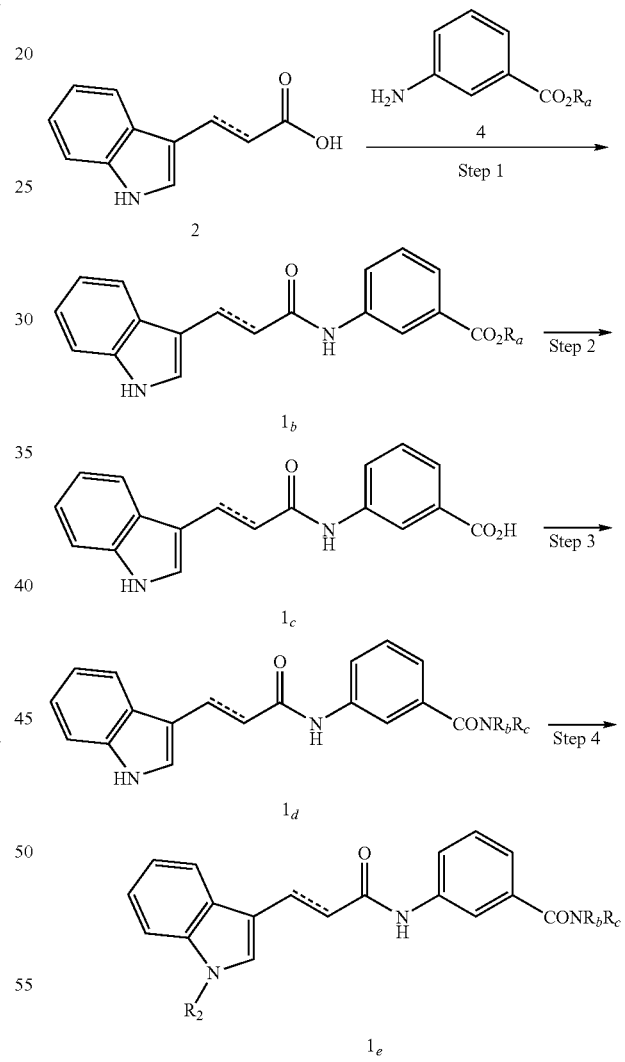

(wherein, $R_a$, $R_b$, $R_c$ and $R_2$ are as defined in Chemical Formula 1, and the derivatives of Chemical Formulas 1b to 1e are included in the indole derivatives of Chemical Formula 1 in accordance with the present invention).

8. The method according to claim 7, wherein, in step 1 or step 3, the amine derivative is 3-amino-benzamide or 3-amino-benzoic acid methyl ester, the organic solvent is dimethylformamide or methylene chloride, the base is diisopropylamine or triethylamine, and the condensing reagent is selected from a group consisting of benzotriazol-1-yl-oxytripyrrolidino-phosphonium hexafluorophosphate (PyBOP), ethylene dichloride (EDC), N-hydroxybenzotriazole (HOBt), O-(benzotriazol-1-yl)-1,1,3,3-tetramethyl uronium hexafluorophosphate (HBTU) and O-(7-azabenzotriazol-1-yl)-N,N,N',N'-tetramethyl uronium hexafluorophosphate (HATU).

9. The method according to claim 7, wherein, in Step 2, the base is lithium hydroxide or sodium hydroxide and the solvent is an organic solvent selected from a group consisting of tetrahydrofuran, dioxane, methanol and ethane, or a mixture of water and the organic solvent.

10. The method according to claim 7, wherein the alkyl amine in step 3 is selected from a group consisting of 2-perfuryl amine, 2-piperidin-1-yl-ethylamine and 3-morpholin-4-yl-propylamine.

11. The method according to claim 7, wherein, in Step 4, the solvent is dimethylformamide or methylene chloride, the base is anhydrous potassium carbonate or anhydrous cesium carbonate, and the $R_2$ is in the form of a halide or an anhydride selected from a group consisting of 2-benzylbromide, 2-dimethylaminoethylchloride, benzylsulfonyl chloride, 2-thiophene chloride, t-butylbromoacetate, di-t-butoxydicarbonate, and acetic anhydride.

* * * * *